United States Patent
Graybeal et al.

(10) Patent No.: US 9,377,358 B2
(45) Date of Patent: Jun. 28, 2016

(54) SPECTROSCOPY SYSTEM USING WAVEGUIDE AND EMPLOYING A LASER MEDIUM AS ITS OWN EMISSIONS DETECTOR

(71) Applicant: EMX International, Inc., Melbourne, FL (US)

(72) Inventors: Daniel Lee Graybeal, Melbourne, FL (US); Alan Carey Rogers, Hickory, NC (US); Andrey Muraviev, Orlando, FL (US)

(73) Assignee: EMX International, Inc., Melbourne, FL (US)

( * ) Notice: Subject to any disclaimer, the term of this patent is extended or adjusted under 35 U.S.C. 154(b) by 0 days.

(21) Appl. No.: 14/792,252

(22) Filed: Jul. 6, 2015

(65) Prior Publication Data

US 2015/0316414 A1    Nov. 5, 2015

Related U.S. Application Data

(63) Continuation of application No. 13/998,751, filed on Dec. 3, 2013, now Pat. No. 9,075,001.

(60) Provisional application No. 61/740,569, filed on Dec. 21, 2012.

(51) Int. Cl.

| | |
|---|---|
| *G01J 5/02* | (2006.01) |
| *G01J 3/10* | (2006.01) |
| *G01J 3/42* | (2006.01) |
| *G01J 3/02* | (2006.01) |
| *G01N 21/3504* | (2014.01) |
| *G01N 21/39* | (2006.01) |

(52) U.S. Cl.
CPC ............... *G01J 3/10* (2013.01); *G01J 3/0205* (2013.01); *G01J 3/0218* (2013.01); *G01J 3/0245* (2013.01); *G01J 3/108* (2013.01); *G01J 3/42* (2013.01); *G01N 21/3504* (2013.01); *G01N 21/39* (2013.01); *G01N 2201/0691* (2013.01); *G01N 2201/0697* (2013.01); *G01N 2201/06113* (2013.01); *G01N 2201/08* (2013.01)

(58) Field of Classification Search
CPC ................ G01N 2021/6484; G01N 21/645; G01N 21/3504; G02B 23/2469
See application file for complete search history.

(56) References Cited

PUBLICATIONS

Curl et al., "Quantum cascade lasers in chemical physics," 2010, Chemical Physics Letters, vol. 487, pp. 1-18.*

* cited by examiner

*Primary Examiner* — Kiho Kim
(74) *Attorney, Agent, or Firm* — Thomas E. Toner; Shumaker, Loop & Kendrick, LLP

(57) ABSTRACT

An intracavity laser absorption infrared spectroscopy system for detecting trace analytes in vapor samples. The system uses a spectrometer in communications with control electronics, wherein the control electronics contain an analyte database that contains absorption profiles for each analyte the system is used to detect. The system can not only detect the presence of specific analytes, but identify them as well. The spectrometer uses a hollow cavity waveguide that creates a continuous loop inside of the device, thus creating a large path length and eliminating the need to mechanically adjust the path length to achieve a high Q-factor. In a preferred embodiment, the laser source may serve as the detector, thus eliminating the need for a separate detector.

14 Claims, 5 Drawing Sheets

SPECTROSCOPY SYSTEM USING WAVEGUIDE AND EMPLOYING A LASER MEDIUM AS ITS OWN EMISSIONS DETECTOR

CROSS REFERENCE TO RELATED APPLICATIONS

This application is a Continuation of U.S. patent application Ser. No. 13/998,751, filed Dec. 3, 2013, which application is a Nonprovisional Application of U.S. Provisional Application No. 61/740,569 filed Dec. 21, 2012; which applications are incorporated by reference as if fully contained herein.

FIELD OF THE INVENTION

The invention relates to the field of intracavity laser absorption spectroscopy. More particularly, the invention relates to intracavity laser absorption infrared spectroscopy for detecting trace analytes.

BACKGROUND OF THE INVENTION

It would be beneficial for different industries including those in the defense, law enforcement, environmental, food, medical, and materials fields to be able to detect trace amounts of gas-phase analytes using a reliable spectroscopic technique. Such a technique would allow them to detect contraband such as drugs, explosives, and/or contaminants on site. Unfortunately, however, very few spectroscopic techniques are sensitive enough to detect trace amounts of gas-phase analytes.

Intracavity laser absorption spectroscopy or "ICLAS" is one of the few spectroscopic techniques capable of doing so. In ICLAS, a test substance is introduced into the cavity of a laser that oscillates across a wavelength range. If the test sample contains a substance that absorbs in the wavelength range emitted by the laser, the absorption features affect the laser spectrum by a measureable amount. ICLAS is very sensitive because it allows for extremely long effective path lengths and high spectral resolution.

Many molecules have a characteristic vibrational and/or rotational absorption spectrum in a particular band of the infrared wavelength region. This band, which ranges from wavelengths of about 3 pm to about 12 pm, is known as the "molecular fingerprint region" because the fundamental rotational/vibrational absorption bands for most molecules fall within these wavelengths. Since each molecule exhibits a unique absorption spectrum in the fingerprint region, it is often used to qualitatively identify molecules.

Quantum cascade lasers or "QCLs" are promising laser sources for performing ICLAS in the infrared wavelength region because they have broad gain spectra, a wide range of wavelengths, high output power, high duty cycle, and the ability operate at room temperature. The fingerprint region is easily accessible with QCLs. Combining a QCL with the ICLAS technique allows one to obtain the highest possible absorption cross-section because of the long path lengths and wavelengths that may be employed.

Unfortunately, conventional intracavity laser absorption spectrometers are not without their drawbacks; namely, their sensitivity it is a function of how well all of their optical components are aligned.

SUMMARY OF INVENTION

These and other aspects, embodiments, and features of the invention will be better understood in the context of the accompanying drawings and the following Detailed Description of Preferred Embodiments.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will convey preferred embodiments of the invention to those skilled in the art.

Figure 1:
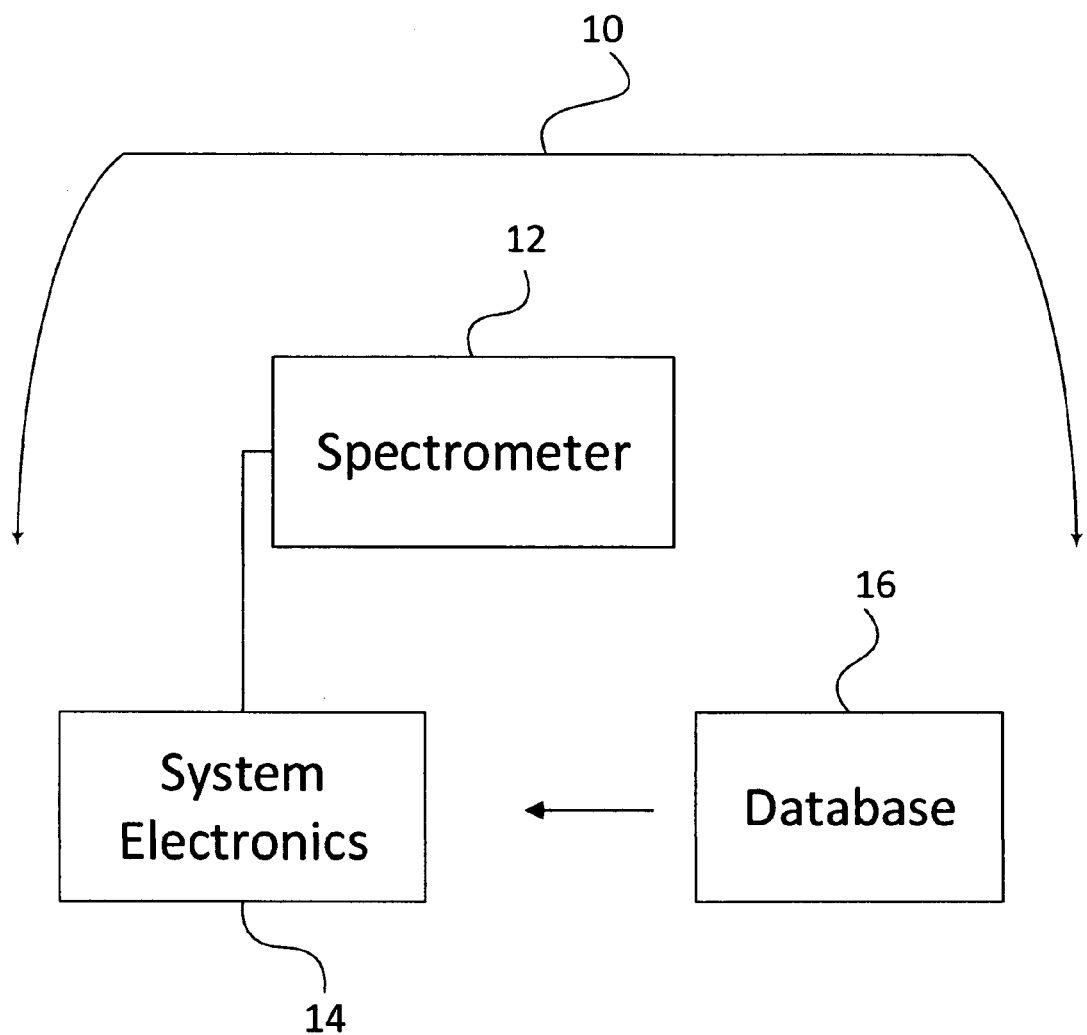
FIG. 1 is a schematic illustration of an infrared spectroscopy system, according to an embodiment of the invention.

An infrared spectroscopy system, in accordance with an embodiment of the invention, is now described with reference to FIG. 1.

The system 10 includes a spectrometer 12 in electronic communication with system electronics 14 for controlling the spectrometer 12 as well as for receiving a signal characteristic of absorption of radiation in the spectrometer 12 by one or more analytes. The system electronics 14 also include one tangible computer memory elements storing machine readable instructions for carrying out the system's 10 functions and one or more computer processors for executing the instructions.

A chemical analysis database 16 containing spectroscopic data for a plurality of chemical analytes is in data communication with the system electronics 14. The spectroscopic data includes absorption profiles for the analytes. When a spectrum is recorded by the spectrometer 12, the system electronics 14 query the spectrum database 16 and determines whether the spectrum corresponds to an absorption profile for an analyte. This enables the system 10 to not only detect the presence of analytes, but also identify them as well. The chemical analysis database 16 allows for the identification of target analytes across a range of concentrations.

The system electronics 14 utilize the spectroscopic data and calculate the probability of a positive detection of an analyte. The probability level that is considered as a positive detection of an analyte is also defined in the database 16.

Figure 2:
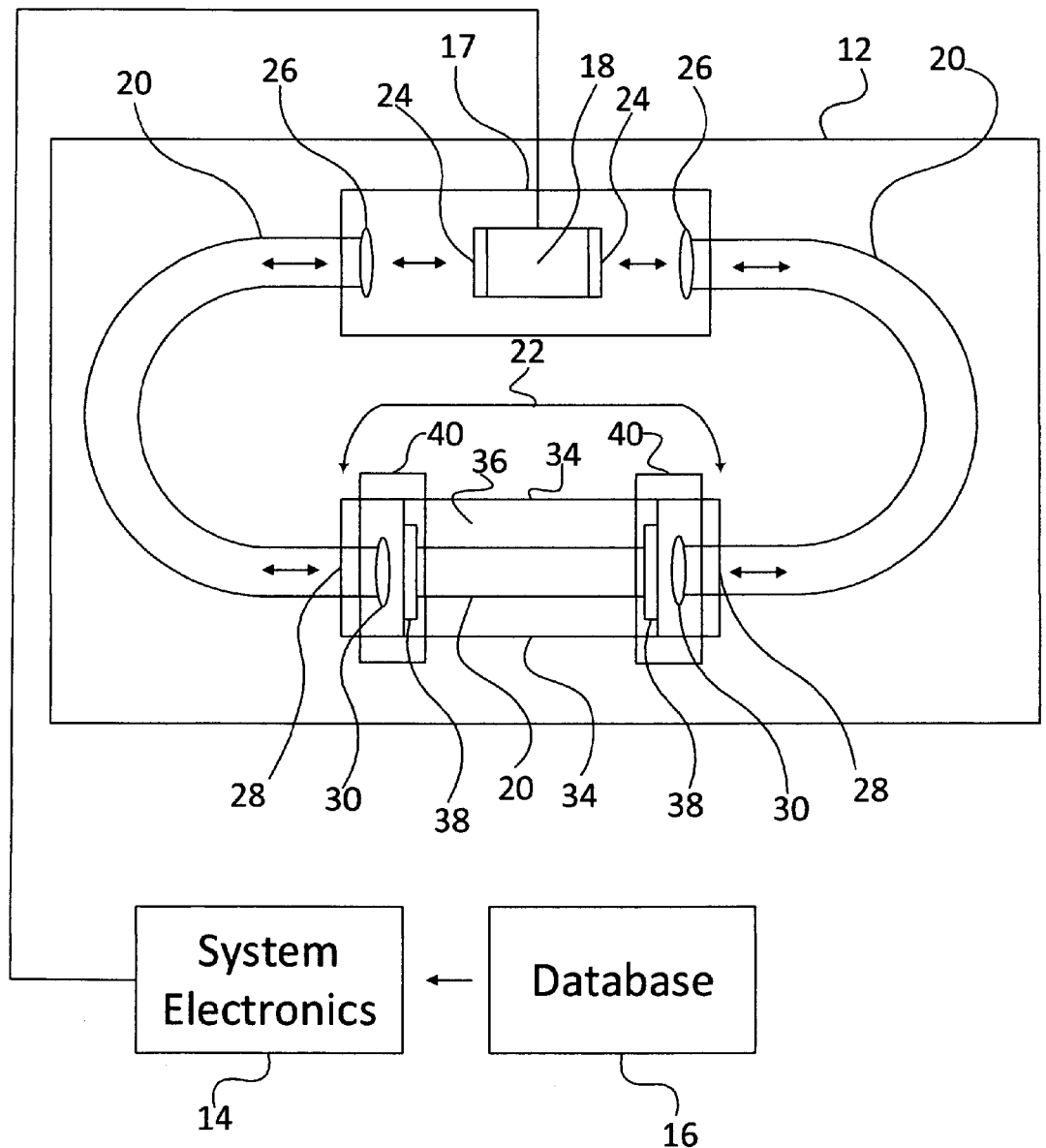
FIG. 2 is a schematic illustration of the infrared spectroscopy system shown in FIG. 1, including additional details of the spectrometer.

Referring to FIG. 2 a preferred embodiment of the spectrometer 12 includes a laser housing 17 mounting a laser source 18, a hollow fiber waveguide 20, and a sample cell 22. The spectrometer 12 is classified as an intracavity laser spectrometer because the test sample is located within a laser cavity defined by the laser source 18 and hollow fiber waveguide 20.

In conventional intracavity laser absorption spectroscopy, one uses a laser cavity with a high quality factor, or "Q-factor", and tunes the cavity by adjusting its length. This is particularly disadvantageous because adjusting the length of the laser cavity introduces mechanical instability. The inventors' spectrometer overcomes this drawback by eliminating the need to adjust the cavity length. This diminishes the Q-factor substantially, but the low Q-factor is counter-balanced by providing a large path length, which is achieved by passing the laser beam through a continuous loop formed by the hollow fiber waveguide 20.

The laser source 18 is capable of emitting infrared radiation in the molecular fingerprint region of the infrared spectrum. More preferably, the laser source 18 is capable of emitting infrared radiation in the wavelength range of from about 3 um to about 4 um. Although use of a QCL is not intended to be limiting, the preferred laser source 18 is a QCL for several reasons; namely, QCLs emit infrared radiation in the preferred wavelength range and allow different infrared wavelengths to be distinguished with high resolution. The opposing facets 24 of the laser source 18 are coated with an anti-reflective coating to minimize internal reflections within the laser source 18 itself.

Hollow fiber waveguides 20 are hollow tubes having an interior surface coated with a highly reflective material. They are typically made of glass, plastic, or sapphire. The coating on the interior is preferably a metal such as gold or silver. Hollow fiber waveguides 20 have losses as low as 0.1 dB/m and may be bent to a desired radius.

When activated, the laser source 18 emits a beam (arrows) through the output facets 24. A pair of optical lenses 26 positioned in the beam path focuses the beam into a hollow fiber waveguide 20, which directs the beam to the sample cell 22. The hollow fiber waveguide 20 is mechanically linked to the sample cell 22 with a connector 28 housing an optical lens 30.

The hollow fiber waveguide 20 directs the laser beam exiting one of the facets 24 in a substantially closed loop onto the other facet 24. This design allows the laser beam to continuously pass through the laser source 18 medium and the sample cell 22, thereby providing a substantially large path length for the laser beam to interact with the sample.

The sample cell 22 includes an outer wall 34 and a sample chamber 36 made of the hollow fiber waveguide 20. The sample to be tested is located in the sample chamber 36. The opposed ends of the sample chamber 36 are sealed with optical windows 38 that are positioned adjacent to the optical lenses 30. In use, the optical lenses 30 focus the beam as it both enters and exits the sample cell 22. A coupler 40 securely couples the connector 28 to the sample cell 22.

In certain embodiments, the sample cell 36 is evacuated and subsequently loaded with the test sample. In these embodiments, it is preferred that the sample chamber 36 be gas tight. In order to exchange one sample for another, a new sample cell 22 containing a new sample may be inserted. The gas to be tested is introduced into the sample chamber 36 via a needle port for allowing the needle of a syringe containing the gas to be inserted therein.

In other embodiments, the system 10 samples the ambient environment in real time by pumping a sample of ambient air into the sample chamber 36. In these embodiments, it is preferred that the sample chamber 36 include an input port for introducing the sample to the sample chamber 36 and an output port for removing the sample from the sample chamber 36. Accordingly, in such embodiments the sample chamber 36 is removable from the spectrometer 12.

The system electronics 14 supply an excitation voltage to the laser source 18, causing it to emit infrared radiation in either pulse or continuous wave mode. When a QCL is used as the laser source 18, it is particularly advantageous to operate in pulse mode because pulsing the QCL causes it to sweep across a large wavelength range. Because the QCL has a temperature dependent wavelength spectrum, the temperature of the QCL determines the wavelengths that QCL emits. The inventors have taken advantage of this property by sweeping across the QCL's emission spectrum by allowing the temperature of the QCL to rise during each pulse.

In preferred embodiments, the lasers source 18 also functions as a detector. This further simplifies the spectrometer 12 relative to conventional systems, which include a detector that is separate from the laser source 18. As the QCL is pulsed, the voltage or current waveform across the QCL medium is modified by the internal modes and amplification phenomena produced by the QCL. As the temperature of the QCL increases during the pulse, the QCL waveform is characterized by a series of peaks.

If the test sample contains an analyte having an absorption band that falls within the wavelength range emitted by the QCL, the absorption band will affect the shape of one or more of the peaks by causing their intensity to either increase or decrease.

Accordingly, each pulse and its corresponding peaks translate to a specific set of wavelengths within the laser cavity. The wavelength and mode may be determined from the temperature of the QCL at the beginning of the pulse as well as the peak location relative to the beginning of the pulse.

Figure 3:
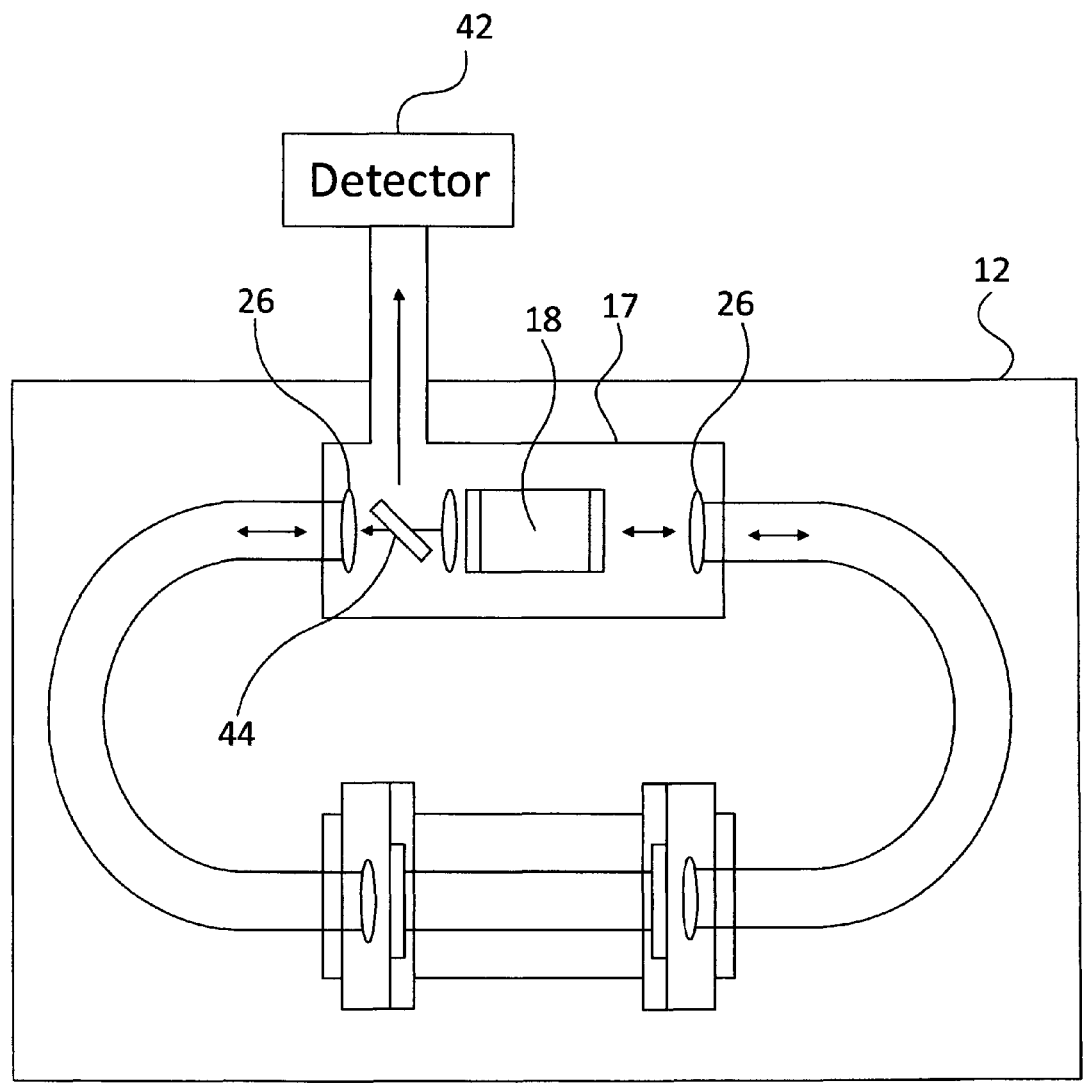
FIG. 3 is a schematic illustration of the infrared spectroscopy system shown in FIG. 2, including an optional detector.

Referring to FIG. 3, the spectrometer 12 optionally includes a detector 42 that is independent from the laser source 18. The detector 42 is optically coupled to the spectrometer by diverting a portion of the beam to the detector through a section of hollow fiber waveguide. The beam is diverted by a mirror 44 placed between the laser source 18 and one of the optical lenses 26 in the laser source housing 17. The detector 42 is adapted to convert the incident laser beam into an analog and/or digital signal that is fed to the system electronics 14. There are various conventional infrared detectors that may be used to suit this purpose, including bolometers, photodiodes, and pyroelectric detectors. In typical applications, however, it is desirable to use a detector 42 that is operable at room temperature. For these applications, an infrared pyroelectric detector may be more suitable.

Figure 4:
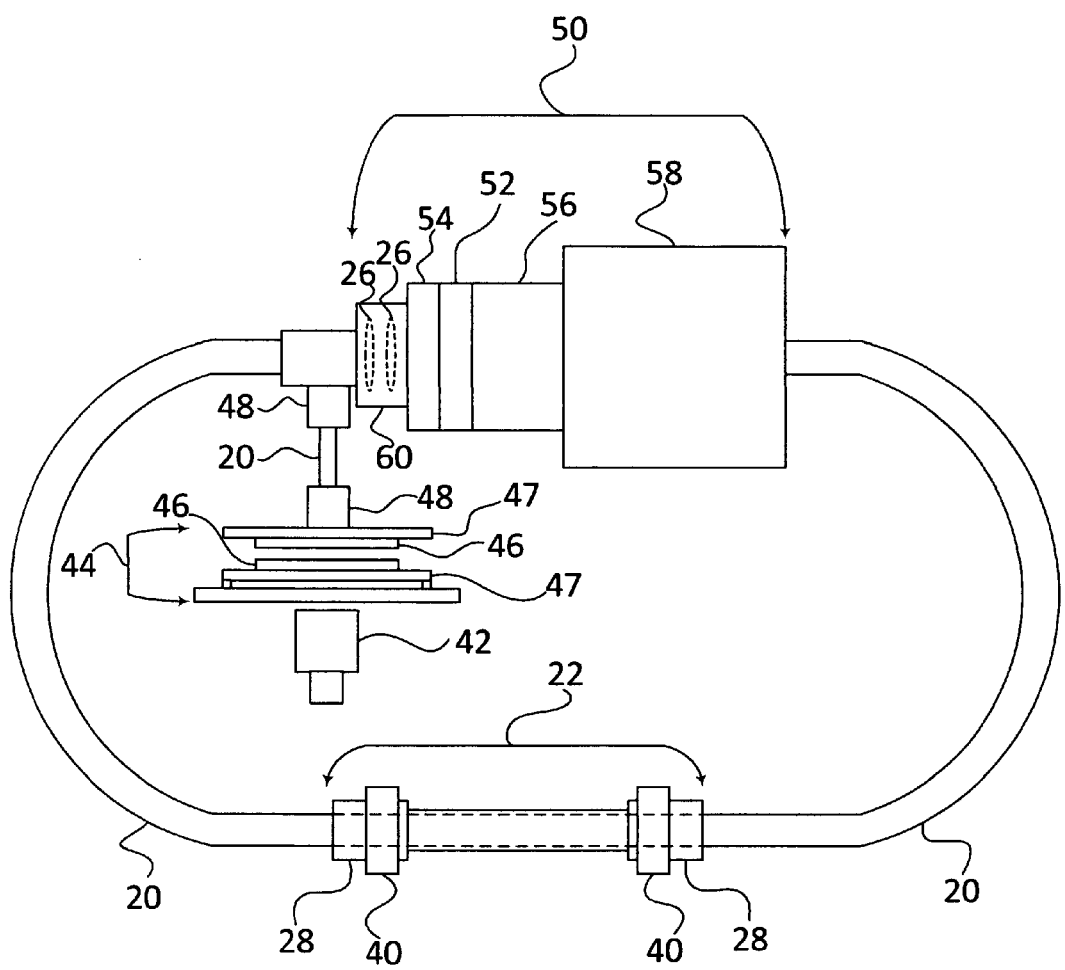
FIG. 4 is a schematic illustration of the infrared spectroscopy system shown in FIG. 3 in which the laser source is mounted on a thermal stage.

Additional details of the spectrometer 12 are shown in FIG. 4 with the optional detector. In the embodiment shown, the detector 42 is in optical communication with a Fabry-Perot resonator 44 that includes a pair of opposed mirrors 46 having adjustable spacing there between. The section of hollow fiber waveguide 20 is connected to the Fabry-Perot resonator 44 and a mounting member 46 using a pair of hollow fiber waveguide connectors 48.

Figure 5:
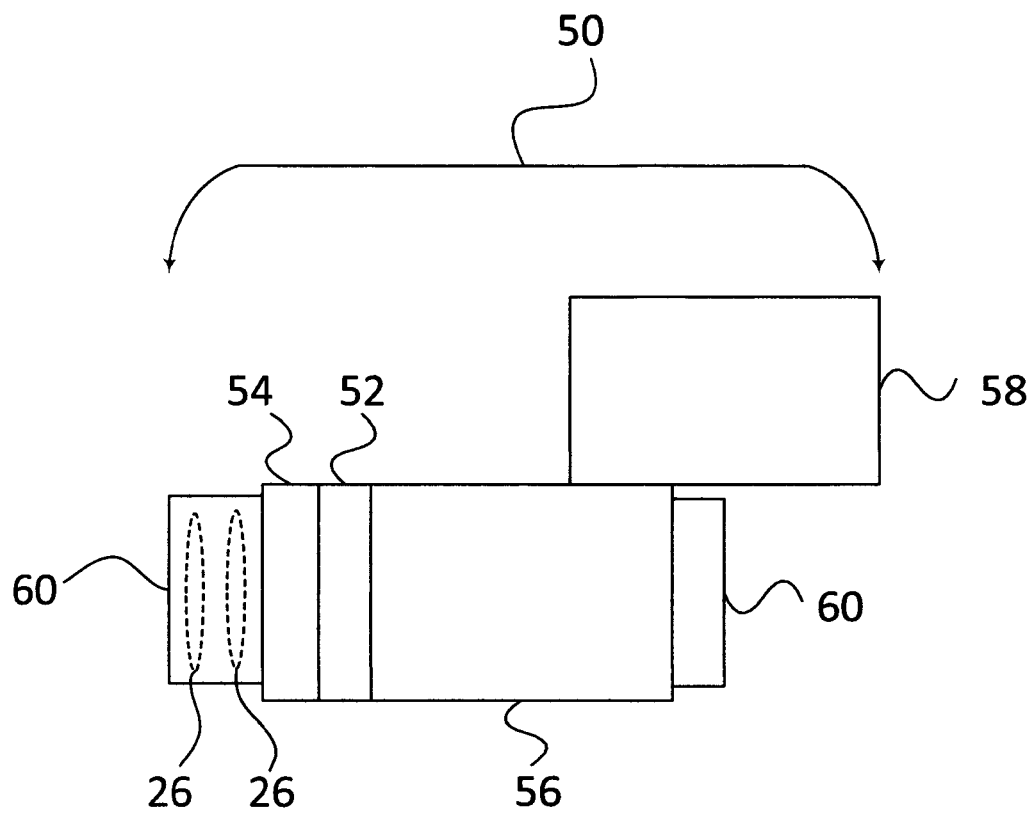
FIG. 5 is a side view of the laser housing, which includes the thermal stage shown in FIG. 4.

Referring also to FIG. 5, the laser source (not shown) is mounted on a thermal stage 50. The thermal stage 50 includes a thermo-electric cooler 52 a heat sink hot side mount 54, a heat sink cold side mount 56, and a radiator 58. The thermal stage 50 is used to control the temperature of the laser source and is in electronic communication with the system electronics 14, which monitor and control the thermal stage 50. The optical lenses 26 positioned adjacent to the laser source are mounted on lens mounts 60.

As discussed above, the system electronics 14 are equipped to control and monitor the spectrometer 12. The system electronics 14 include a power supply for providing power to the laser source 18 as well as the electronic components that control the elements of the spectrometer 12. These electronic components include a thermal stage control module for controlling the thermal stage 50, a laser source drive module for controlling the laser source 18 and detecting the electrical waveform during electrical excitation, a Fabry-Perot resonator control module for adjusting the spacing between the mirrors of the Fabry-Perot resonator 44, a detector control module for controlling the detector and receiving a signal from the detector, and an auxiliary control module for controlling other auxiliary system components. Auxiliary system components may include, for example, controls for pumps, valves or other devices that are optionally included with the system 10.

The system electronics 14 also include one or more data acquisition devices such as an oscilloscope, an A/D converter, photon counter, and or a signal integrator. Data analysis electronics in data communication with the data acquisition devices include one or more computer processors that determine values of various parameters of interest from signals characterizing the interaction of the test sample with the emitted beam. These parameters preferably include, but are not limited to: wavelength or frequency of the beam, absorption spectra, laser gain parameters, laser emission spectra, time dependence of the laser emission spectrum, and radiation intensity.

Preferably, all of the components of the infrared spectroscopy system 10, including the spectrometer 12, the system electronics 14, and the chemical analysis database 16 are securely contained together in a robust system housing that can easily be transported. Because of the system's 10 design, it can sustain mechanical shocks and vibrations without giving rise to the need to adjust or realign any of its optical components.

Certain preferred embodiments of the system 10 do not require the use of a pump to evacuate the sample cell 22 or the hollow fiber waveguide 20, thereby eliminating another of the drawbacks of conventional intracavity laser absorption spectrometers.

In these embodiments, the laser emission wavelengths are between about 3 pm to about 4 pm, which is outside of where the absorption bands for water and carbon dioxide fall. Advantageously, the inventors found that many target analytes exhibit absorption bands 3 μm to 4 μm range. The infrared spectroscopy system 10 has many advantageous uses. Some, but not all, of its uses are now described.

In general, the system 10 can be used in any environment in which detecting and/or identifying gas phase analytes is important. Exemplary uses include the detection of chemicals used to prepare explosives, drugs, impurities in food, or other types of contraband.

The system 10 may also be used to detect biomarkers from breath samples. In this example, a person breathes a breath sample into a bag. The breath sample is then extracted from the bag and introduced into the sample chamber 36. The system 10 then records a spectrum of the breath sample and the system electronics 14 compare the spectrum to the spectroscopic data in the database 16 to determine whether a specific biomarker is present. The presence of specific biomarkers in the breath sample is an indicator that the person may have a specific physical condition.

Accordingly, use of the system 10 in this manner will assist medical professionals in diagnosing and treating patients.

In another particular use, the system 10 functions as an air sampler at a facility prone to contamination by airborne hazardous chemicals, such as chemical plants or the like. In this example, the system 10 periodically samples the air at the facility by drawing the ambient air into the sample chamber 36. It then records a spectrum of the ambient air and compares the spectrum to the spectroscopic data in the database 16. If a particular target analyte is detected, the system 10 sends an alert signal to the personnel at the facility.

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. Any materials, which may be cited above, are fully incorporated herein by reference.

It is also to be understood that the following claims are intended to cover all of the generic and specific features of the invention herein described, and all statements of the scope of the invention which, as a matter of language, might be said to fall therebetween. Relative terminology, such as "substantially" or "about," describe the specified materials, steps, parameters or ranges as well as those that do not materially affect the basic and novel characteristics of the claimed inventions as whole (as would be appreciated by one of ordinary skill in the art). Now that the invention has been described,

What is claimed is:

1. A spectroscopy system comprising:
  a) a quantum cascade laser (QCL) having a pair of output facets that are optically coupled in such a way that an electromagnetic beam exiting each of the facets passes through a hollow fiber waveguide that directs the beam onto the other facet;
  b) a sample chamber positioned along the hollow fiber waveguide;
  c) an excitation energy source for driving said QCL with a constant current;

d) data acquisition electronics for measuring a QCL waveform as the electromagnetic beam passes through the sample chamber; and e) a controller coupled to said data acquisition electronics for dynamically detecting the presence of an analyte in the sample chamber responsive to at least one detection signal resulting from the interaction between an analyte in the sample chamber and the electromagnetic beam by monitoring the current supplied by the excitation energy source.

2. The spectroscopy system of claim 1 wherein the constant current comprises a plurality of constant current pulses.

3. The spectroscopy system of claim 1 wherein the at least one detection signal comprises a voltage waveform across the QCL based upon a varying impedance of said QCL.

4. The spectroscopy system of claim 3 wherein the voltage waveform includes a plurality of spikes due to variations during application of the constant current to said QCL; and wherein said controller detects the presence of the analyte based upon magnitudes of the plurality of spikes.

5. The spectroscopy system of claim 3 wherein said controller detects the presence of the analyte in the sample chamber based upon a minimum value in the voltage waveform during application of the constant current to the QCL.

6. A spectrometer comprising:
a) a sample chamber having at least one vapor sample therein;
b) a quantum cascade laser (QCL) comprising:
 i) a QCL crystal having a first and second emitting facet for providing an electromagnetic beam, and an active region adjacent each of said emitting facets;
 ii) a hollow fiber waveguide having a first end adjacent the first emitting facet of the QCL crystal ad a second end adjacent the second emitting facet;
 iii) an optical cavity comprising at least one mirror being external to said QCL crystal, and for redirecting the electromagnetic beam into the active region of said QCL crystal to provide optical feedback,
 iv) the sample chamber being positioned to allow the electromagnetic beam within said hollow fiber to pass through there through;
 v) an excitation energy source to provide the QCL crystal with a constant current; and
 iv) a controller coupled to said QCL to determine absorption by the at least one vapor sample in the sample chamber based upon at least one detection signal from said QCL crystal.

7. The spectrometer of claim 6 wherein the constant current comprises a plurality of constant current pulses.

8. The spectrometer of claim 6 wherein the at least detection error signal comprises a voltage waveform across said QCL crystal based upon a varying impedance of said QCL crystal.

9. The spectrometer of claim 8 wherein the voltage waveform includes a plurality of spikes due to mode changes during application of the constant current to said QCL crystal; and wherein said controller determines absorption by the at least one vapor sample in the sample chamber based upon magnitudes of the plurality of spikes.

10. The spectrometer of claim 9 wherein controller determines absorption by the at least one vapor sample in the sample chamber based upon a minimum value in the voltage waveform during application of the constant current to said QCL crystal.

11. A method of operating a quantum cascade laser (QCL) comprising:
a) providing a QCL crystal having:
 i) a first and second emitting facet, and an active region adjacent at least one emitting facet, the at least one emitting facet for providing an electromagnetic beam;
 ii) a hollow fiber waveguide having a first end adjacent the first emitting facet for directing the electromagnetic beam into a sample chamber, and;
 iii) a QCL excitation source for providing the QCL crystal with a constant current; and
B) determining the absorption by the at least one vapor sample in the sample chamber based upon at least one detection signal from said QCL crystal.

12. The method of claim 11 wherein the constant current comprises a plurality of constant current pulses.

13. The method of claim 12 wherein the at least one error signal comprises a voltage waveform across the QCL crystal based upon a varying impedance of the QCL crystal.

14. The method of claim 13 wherein the voltage waveform includes a plurality of spikes due to mode-changes during application of the constant current to the QCL crystal.

* * * * *